(12) United States Patent
Isla Garcia et al.

(10) Patent No.: US 12,702,379 B2
(45) Date of Patent: Aug. 11, 2026

(54) DEFORMABLE SENSOR WITH DEFORMATION FEEDBACK, AND SYSTEM AND METHOD USING THE SAME

(71) Applicant: EDWARDS LIFESCIENCES CORPORATION, Irvine, CA (US)

(72) Inventors: Julio Agustin Isla Garcia, Irvine, CA (US); Rendle Lamarr Myles, Jr., Covina, CA (US); Xiaolong Li, Irvine, CA (US); Alexander H. Siemons, Yorba Linda, CA (US); Blake W. Axelrod, Sierra Madre, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 97 days.

(21) Appl. No.: 18/181,508

(22) Filed: Mar. 9, 2023

(65) Prior Publication Data

US 2023/0210496 A1 Jul. 6, 2023

Related U.S. Application Data

(63) Continuation of application No. PCT/US2021/049735, filed on Sep. 9, 2021.

(60) Provisional application No. 63/077,451, filed on Sep. 11, 2020.

(51) Int. Cl.
*A61B 8/00* (2006.01)

(52) U.S. Cl.
CPC .......... *A61B 8/4254* (2013.01); *A61B 8/4455* (2013.01); *A61B 8/4477* (2013.01); *A61B 8/54* (2013.01)

(58) Field of Classification Search
CPC ... A61B 8/4227; A61B 8/4236; A61B 8/4245; A61B 8/4254; A61B 8/4263; A61B 8/4444; A61B 8/4455; A61B 8/4477; A61B 8/4494; A61B 8/54
See application file for complete search history.

(56) References Cited

U.S. PATENT DOCUMENTS

2019/0046158 A1* 2/2019 Kroon .................. A61B 8/4236
2020/0253554 A1* 8/2020 Schumann ........... A61B 5/6833

FOREIGN PATENT DOCUMENTS

WO WO-2007023426 A2 * 3/2007 ......... A61B 5/02125
WO WO-2019152246 A1 * 8/2019 ........... A61B 8/4236

* cited by examiner

*Primary Examiner* — Michael J Carey
*Assistant Examiner* — Maria Christina Talty
(74) *Attorney, Agent, or Firm* — Getz Balich LLC

(57) ABSTRACT

A biomedical sensor is provided that includes a deformable body panel, a first ultrasonic transducer, a second ultrasonic transducer, and a displacement sensor. The first and second ultrasonic transducers are attached to, and the displacement sensor is in communication with, the deformable body panel. The biomedical sensor is disposable in at least one default configuration wherein the first and second ultrasonic transducers are disposed relative to one another in a known first spatial transducer configuration. The biomedical sensor is disposable in one or more deformed configurations wherein the first and second ultrasonic transducers are disposed relative to one another in a second spatial transducer configuration different than the first spatial transducer configuration. The at least one displacement sensor is configured to produce signal information indicative of a difference between the first and second spatial transducer configurations.

9 Claims, 13 Drawing Sheets

DEFORMABLE SENSOR WITH DEFORMATION FEEDBACK, AND SYSTEM AND METHOD USING THE SAME

RELATED APPLICATION

This application claims the benefit of PCT/US2021/049735 filed on Sep. 9, 2021, which claims priority based on U.S. Provisional Patent Application Ser. No. 63/077,451, filed Sep. 11, 2020, and entitled DEFORMABLE SENSOR WITH DEFORMATION FEEDBACK, AND SYSTEM AND METHOD USING THE SAME, the complete disclosures of which are hereby incorporated herein in their entireties.

BACKGROUND OF THE INVENTION

1. Technical Field

The present disclosure relates to systems and methods for ultrasonically sensing tissue in general, and to systems and methods utilizing deformable ultrasonic sensors in particular.

2. Background Information

Tissue sensors having a plurality of ultrasonic transducers operable to emit and receive ultrasonic signals may be used to provide information regarding the tissue being sensed. In some applications, the information produced is sensitive to the relative positions and/or orientations of the ultrasonic transducers. A sensor that is pliable to conform to a subject's tissue can be bent from an initial/default orientation when attached to the subject, and the relative positions and/or orientations of the ultrasonic transducers changed from the initial/default orientation. Since the information derived from the sensor may be a function of the relative positions and/or orientations of the ultrasonic transducers, unknown deviations from the planar orientation can introduce undesirable error into the information.

What is needed is a system and method that is capable of determining the actual relative positions and/or orientations of the ultrasonic transducers, and that can account for the same as necessary.

SUMMARY

According to an aspect of the present disclosure, a biomedical sensor is provided that includes a deformable body panel, at least one first ultrasonic transducer, at least one second ultrasonic transducer, and at least one displacement sensor. The at least one first ultrasonic transducer and the at least one second ultrasonic transducer are attached to the deformable body panel. The at least one displacement sensor is in communication with the deformable body panel. The biomedical sensor is disposable in at least one default configuration wherein the at least one first ultrasonic transducer and the at least one second ultrasonic transducer are disposed relative to one another in a known first spatial transducer configuration. The biomedical sensor is disposable in one or more deformed configurations wherein the at least one first ultrasonic transducer and the at least one second ultrasonic transducer are disposed relative to one another in a second spatial transducer configuration different than the known first spatial transducer configuration. The at least one displacement sensor is configured to produce signal information indicative of a difference between the known first spatial transducer configuration and the second spatial transducer configuration.

In any of the aspects or embodiments described above and herein, the at least one displacement sensor may include a plurality of displacement sensors configured to sense a difference between relative positions of the at least one first ultrasonic transducer and the at least one second ultrasonic transducer within the known first spatial transducer configuration, and the relative positions of the at least one first ultrasonic transducer and the at least one second ultrasonic transducer within the one or more deformed configurations.

In any of the aspects or embodiments described above and herein, the plurality of displacement sensors may be configured to sense a difference between relative orientations of the at least one first ultrasonic transducer and the at least one second ultrasonic transducer within the known first spatial transducer configuration, and relative orientations of the at least one first ultrasonic transducer and the at least one second ultrasonic transducer within the one or more deformed configurations.

In any of the aspects or embodiments described above and herein, the biomedical sensor may further include a processor chip in communication with the plurality of displacement sensors.

In any of the aspects or embodiments described above and herein, the at least one displacement sensor may include a plurality of displacement sensor cells, each having a plurality of displacement sensors, the plurality of displacement sensor cells spaced apart from one another and attached to the deformable body panel.

In any of the aspects or embodiments described above and herein, the at least one displacement sensor may include interdigital elements configured to sense bending of the sensor, or buckling of the sensor, or both.

In any of the aspects or embodiments described above and herein, the biomedical sensor may be configured to assume the at least one default configuration in the absence of external forces acting on the sensor.

In any of the aspects or embodiments described above and herein, the deformable body panel may be a solid body.

According to another aspect of the present disclosure, a biomedical system is provided that includes at least one biomedical sensor as described above and herein, and a controller. The controller in communication with the at least one biomedical sensor and a memory storing instructions, which instructions when executed cause the controller to: a) determine the difference between the known first spatial transducer configuration and the second spatial transducer configuration using the signal information from the at least one displacement sensor; and b) produce information representative of the relative positions of the at least one first ultrasonic transducer and the at least one second ultrasonic transducer within the one or more deformed configurations using the determined difference.

In any of the aspects or embodiments described above and herein, the instructions when executed may cause the controller to produce information representative of the relative orientations of the at least one first ultrasonic transducer and the at least one second ultrasonic transducer within the one or more deformed configurations using the determined difference.

In any of the aspects or embodiments described above and herein, the instructions when executed cause the controller to produce information relating to blood vessel diameter, or pulse wave velocity, or both, using the information representative of the relative positions of the at least one first ultrasonic transducer and the at least one second ultrasonic transducer within the one or more deformed configurations.

According to another aspect of the present disclosure, a method of using a deformable biomedical sensor is provided. The method includes: a) providing a biomedical sensor having a deformable body panel, at least one first ultrasonic transducer attached to the deformable body panel, at least one second transducer attached to the deformable body panel, and at least one displacement sensor in communication with the deformable body panel, wherein the at least one biomedical sensor is disposable in at least one default configuration wherein the at least one first ultrasonic transducer and the at least one second ultrasonic transducer are disposed relative to one another in a known first spatial transducer configuration; b) attaching the biomedical sensor to a subject's skin in an applied configuration, wherein in the applied configuration the at least one first ultrasonic transducer and the at least one second ultrasonic transducer are disposed relative to one another in a second spatial transducer configuration; c) using the at least one displacement sensor to determine any difference between the first spatial transducer configuration and the second spatial transducer configuration; and d) producing information representative of the relative positions of the at least one first ultrasonic transducer and the at least one second ultrasonic transducer within the one or more deformed configurations using the determined difference.

In any of the aspects or embodiments described above and herein, the step of producing information representative of the relative positions of the at least one first ultrasonic transducer and the at least one second ultrasonic transducer may include producing information representative of the relative orientations of the at least one first ultrasonic transducer and the at least one second ultrasonic transducer within the second spatial transducer configuration, or the relative positions of the at least one first ultrasonic transducer and the at least one second ultrasonic transducer within the known first spatial transducer configuration, and relative positions of the at least one first ultrasonic transducer and the at least one second ultrasonic transducer within the second spatial transducer configuration.

In any of the aspects or embodiments described above and herein, the method may further include producing information relating to blood vessel diameter, or pulse wave velocity, or both, using the information representative of the relative orientations of the at least one first ultrasonic transducer and the at least one second ultrasonic transducer within the applied configuration, or the information representative of the relative positions of the at least one first ultrasonic transducer and the at least one second ultrasonic transducer within the applied configuration, or both.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

FIG. 9B shows a longitudinal shear stress load applied in a first direction, and FIG. 9C shows a longitudinal shear stress load applied in a second direction, opposite the first direction. FIG. 9D shows a longitudinal shear stress load applied in a third direction, perpendicular to the first and second directions.

FIG. 15B diagrammatically illustrates the biomedical sensor shown in FIG. 15A in a configuration deformed from the default configuration with the deformed configuration unaccounted for.

FIG. 15C diagrammatically illustrates the biomedical sensor shown in FIG. 15A in a configuration deformed from the default configuration with the deformed configuration accounted for.

DETAILED DESCRIPTION

Figure 1:
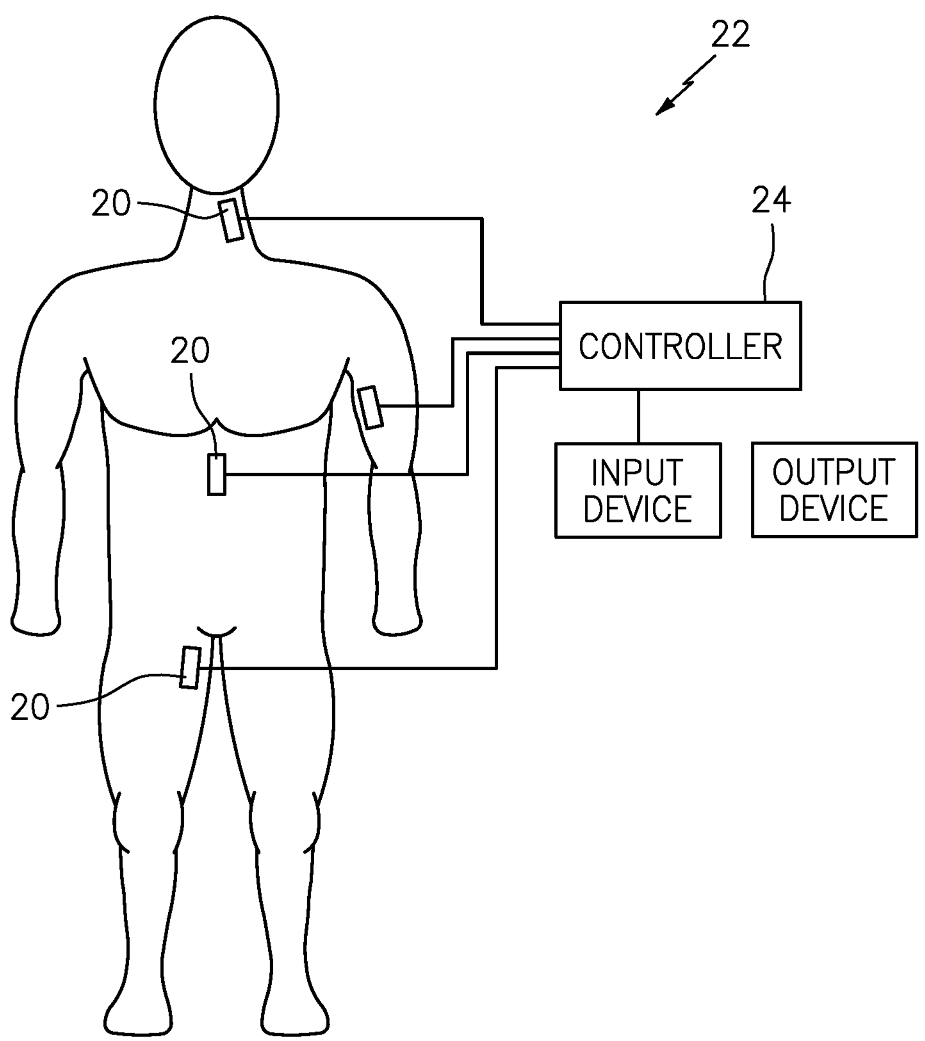
FIG. 1 is a diagram of the present disclosure system, illustrating biomedical sensors attached to a subject.

Referring to FIG. 1, aspects of the present disclosure include a biomedical sensor 20 that may be worn by a subject, a system 22 for non-invasively sensing tissue using one or more biomedical sensors 20, and a method for non-invasively sensing tissue using one or more biomedical sensors 20. As described herein, the biomedical sensor 20 includes a plurality of ultrasonic transducers 26 (e.g., see FIGS. 3-4) and is configured to sense the relative positions and/or orientations of the ultrasonic transducers 26. The biomedical sensor 20 may be described as having a "default" configuration wherein the relative positions and/or orientations of the ultrasonic transducers 26 are known. A default configuration for a biomedical sensor 20 may be the configuration the sensor 20 assumes in the absence of any forces acting on the sensor 20, but the present disclosure is not limited to a default configuration being the sensor "at rest" configuration. A biomedical sensor 20 may have one or more alternative default configurations wherein the relative positions and/or orientations of the ultrasonic transducers 26 are known. Alternatively, the present disclosure system may be configured to determine displacement sensor 28 values in a first configuration (which may then be considered to be the default configuration) and then sense deformation of the biomedical sensor 20 from that first configuration based on input from the deformation sensors 28. If the biomedical sensor 20 is deformed into a configuration other than the default configuration (e.g., bent or stretched when applied to a tissue surface), the sensor 20 is configured to sense the relative positions and/or orientations of the ultrasonic transducers 26 in the deformed configuration (e.g., deviations from the default configuration) and provide information regarding the same. The system 22 includes the one or more biomedical sensors 20 and a controller 24. FIG. 1 diagrammatically illustrates a present disclosure system 22 with a plurality of biomedical sensors 20 disposed on a subject, which sensors 20 are in communication with a controller 24.

The controller 24 is in signal communication with the biomedical sensor(s) 20 to perform the functions described herein. The controller 24 may include any type of computing device, computational circuit, processor(s), CPU, computer, or the like capable of executing a series of instructions that are stored in memory. The instructions may include an operating system, and/or executable software modules such as program files, system data, buffers, drivers, utilities, and the like. The executable instructions may apply to any functionality described herein to enable the system 22 to accomplish the same algorithmically and/or coordination of system 22 components. The controller 24 may include a single memory device or a plurality of memory devices. The present disclosure is not limited to any particular type of non-transitory memory device, and may include read-only memory, random access memory, volatile memory, non-volatile memory, static memory, dynamic memory, flash memory, cache memory, and/or any device that stores digital information. The controller 24 may include, or may be in communication with, an input device that enables a user to enter data and/or instructions, and may include, or be in communication with, an output device configured, for example to display information (e.g., a visual display or a printer), or to transfer data, etc. Communications between the controller 24 and other system components may be via a hardwire connection or via a wireless connection.

Each biomedical sensor 20 includes a plurality of ultrasonic transducers 26, at least one displacement sensor 28, and a body panel 30. Each ultrasonic transducer 26 is configured to both transmit and receive ultrasonic signals; e.g., an ultrasonic transducer 26 may include one or more elements that both transmit and receive ultrasonic signals, or may include one or more elements dedicated to transmitting ultrasonic signals and one or more elements dedicated to receiving ultrasonic signals. In those instances wherein an ultrasonic transducer includes a plurality of elements, those elements may be arranged in an array. The ultrasonic transducers 26 may be configured for two-way signal communication with the controller 24 via hard wire or by wireless means. The term "ultrasonic signals" as used herein refers to the mechanical pressure waves produced and/or received by the ultrasonic transducer 26, which pressure waves are sometimes referred to as pressure waves, sound waves, sound pulses, acoustic waves, or the like. The ultrasonic transducers 26 are configurable to produce the ultrasonic signals at one or more predetermined frequencies and wavelengths; e.g., typically within the range of 1-10 MHz. Non-limiting examples of acceptable ultrasonic transducer 26 types include transducers having piezoelectric elements; e.g., PZT (lead zirconate titanate) based transducers, CMUT (capacitive micromachine) transducers, PMUT (piezoelectric micromachine) transducers, and like devices operable to transform mechanical energy into electrical energy and vice versa.

Figure 2:
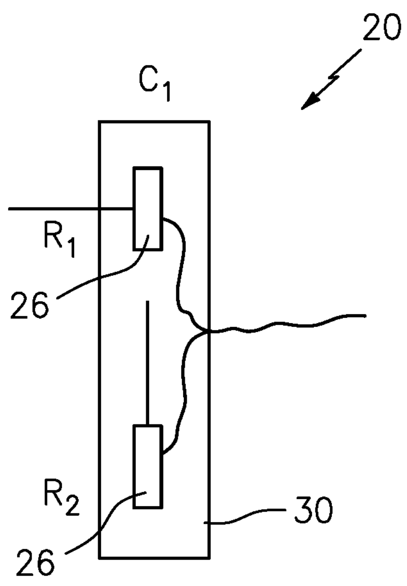
FIG. 2 is a diagrammatic view of a biomedical sensor embodiment.
Figure 3:
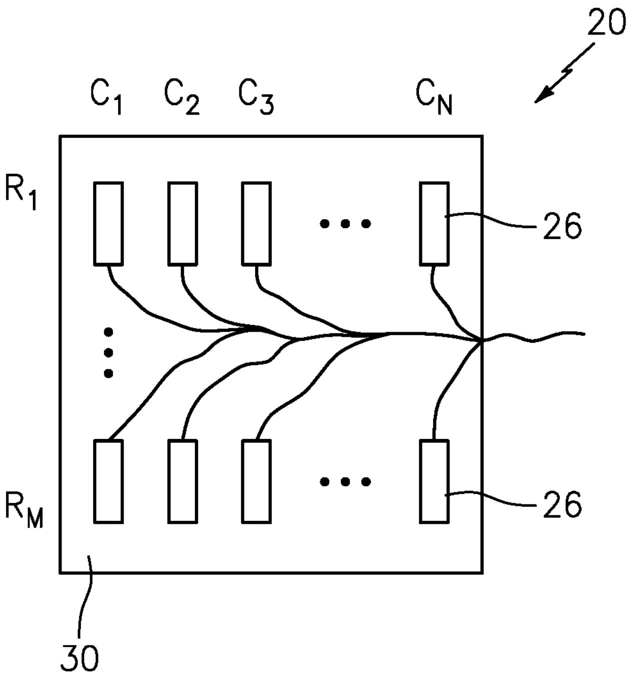
FIG. 3 is a diagrammatic view of a biomedical sensor embodiment.

When the biomedical sensor 20 is disposed in a default configuration, the plurality of ultrasonic transducers 26 are disposed in a geometric configuration wherein the relative positions and/or orientations of the transducers 26 are known. For example, in some embodiments the ultrasonic transducers 26 may be disposed in a two-dimensional (2D) array. An example of such an array is shown in FIG. 2; e.g., a transducer 26 array having one column ($C_1$) and two rows ($R_1$, $R_2$), wherein the distance between the rows is known. In the default configuration, the distance between rows may be uniform. Another example of a two dimensional transducer 26 array configuration is shown in FIG. 3, which array includes a plurality of columns and a plurality of rows; e.g., "N" number of columns ($C_1$, $C_2$, $C_3$ . . . $C_N$), with each column having "M" number of rows ($R_1$ . . . $R_M$), where "N" and "M" are integers. Here again, the intercolumn distances and the interrow distances are known. In the default configuration, the distances between transducers in a column may be uniform, and the distance between transducers in a row may be uniform. U.S. Provisional Patent Application No. 63/054,558, filed Jul. 21, 2020, entitled "System and Method for Non-Invasively Sensing a Blood Vessel", assigned to the present applicant, discloses biomedical sensor 20 configurations like those described above, and is hereby incorporated by reference in its entirety. As indicated above, the above-described ultrasonic transducer 26 array configurations are examples of 2D transducer 26 configurations wherein the relative positions and/or orientations are known when the biomedical sensor 20 is disposed in its default configuration; e.g., the position of the ultrasonic transducers 26 may be described in terms of "X" and "Y" coordinates, where X and Y are orthogonal axes defining an X-Y plane. The present disclosure is not limited to these examples. For example, a biomedical sensor 10 may have a three-dimensional (3D) default configuration; e.g., the relative positions and/or orientations of the ultrasonic transducers 26 are known and describable in terms of X, Y, and Z orthogonal axes. To be clear, the geometric configuration of ultrasonic transducers 26, where the relative positions and/or orientations of the transducers 26 is known refers to ultrasonic transducers that may include a plurality of elements as described above. However, if an individual ultrasonic transducer 26 does include an array of elements and the relative positions and/or orientations of the elements within the transducer 26 are known, then the present disclosure may be utilized to determine position and/or orientation changes between elements within a transducer 26.

Each ultrasonic transducer 26 may be described as having an active area. The active area is the surface of the transducer 26 from which ultrasonic signals emanate and/or are accepted or received. The ultrasonic transducers 26 that are used within the present disclosure are not limited to any particular active area configuration; e.g., circular, oblong, etc.

The ultrasonic transducers 26 may be configured to project ultrasonic signals in a variety of different configurations, and the present disclosure is not limited to any particular configuration. For description purposes herein, the ultrasonic signals projected by each ultrasonic transducer 26 will be described as being projected in the form of an incident beam having an intensity profile that is a function of the angle between the direction of interest and the central axis that extends out normal to the active surface of the transducer 26 and is centered on the latter. This intensity profile can take a plurality of shapes determined by the size and excitation of the active surface. Preferably, ultrasonic transducers used with the present disclosure have a profile that maximizes the detection of the features of interest. Examples of such profiles may include plane wave approximations, pencil beams, raised cosines and the like. In some applications, the ultrasound transducers 26 may be operated to produce an incident beam of ultrasonic signal configured to permit the features of a blood vessel (e.g., the posterior and anterior walls of an artery) to be identified and located relative to one another. The ultrasonic transducers 26 may be operated to produce the aforesaid ultrasonic signals a plurality of times during a cardiac cycle. The ultrasonic signals that form the incident beam reflect off of elements within the tissue, including the anterior and posterior walls of the artery being investigated. The reflected ultrasonic signals reflect back towards and are sensed by the ultrasonic transducers 26. The ultrasonic transducers 26, in turn, produce electronic signals that are communicated to the controller 24. The features within the reflected signals that correspond to the anterior and posterior walls of the artery may be extracted from all of the reflected signals by the controller 24 using stored instructions. The reflected ultrasonic signals that correspond to the anterior and posterior walls of the artery permit the determination of useful physiologic information; e.g., arterial diameter, pulse wave velocity, etc.

Figure 4:
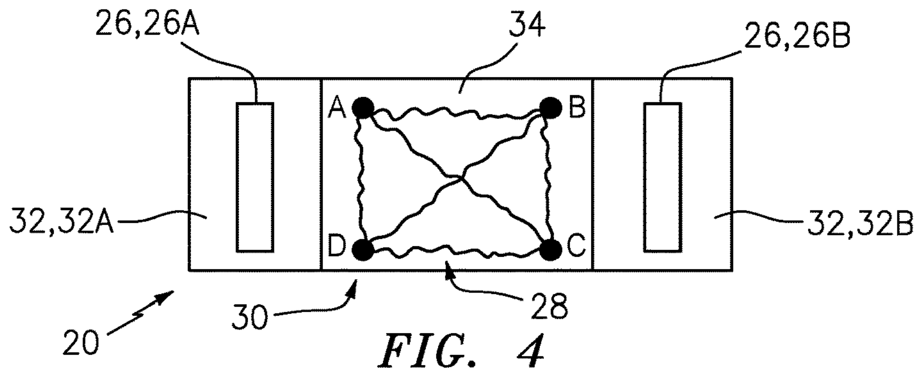
FIG. 4 is a diagrammatic view of a biomedical sensor embodiment.
Figure 18:
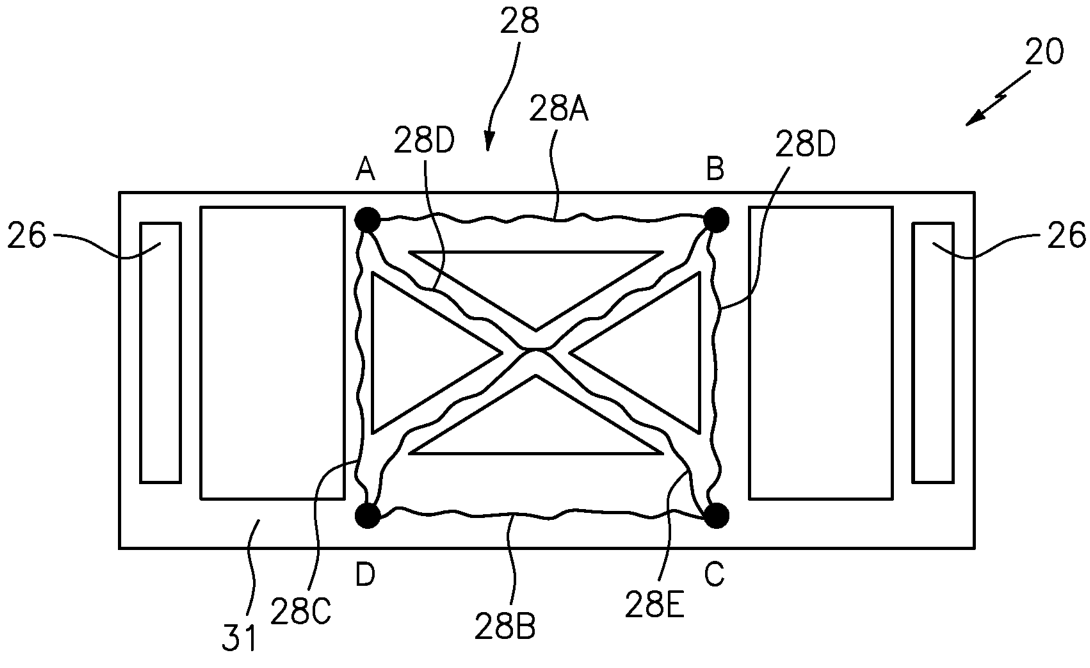
FIG. 18 is diagrammatic view of a biomedical sensor embodiment.

The body panel 30 is configured to maintain the ultrasonic transducers 26 in a default configuration when no forces are applied to the body panel 30. For example, the body panel 30 may be configured to maintain the ultrasonic transducers in a 2D planar default configuration wherein the positions of the ultrasonic transducers 26 (e.g., $X_1$, $Y_1$, $X_2$, $Y_2$, etc.) are known and the orientation of each transducer 26 is known (e.g., the orientation of the beam projected by the transducer 26 is known). The body panel 30 is sufficiently deformable (e.g., flexible and/or stretchable) to permit the biomedical sensor 20 to sufficiently deform from its default configuration to conform to the subject's skin surface. The body panel 30 may be elastically or plastically deformable. In some embodiments, the body panel 30 may be a solid body, and may have cavities or apertures for receiving components (e.g., ultrasonic transducers 26, displacement sensors 28, circuitry, etc.) The present disclosure is not, however, limited to a body panel 30 having a solid body. The term "solid body" is used herein to describe a body without substantial cavities or apertures, other than those that may be used for components. A solid body may be formed from a sponge or foam material that inherently includes some voids. A solid body may be formed with a homogeneous material, or a non-homogeneous material; e.g., a laminate structure. As an alternative to a solid body, the body panel 30 may include a deformable frame 31 (e.g., See FIG. 18) operable to maintain the ultrasonic transducers 26 in the default configuration. An example of a solid body base panel material is one comprising a silicone elastomeric material. The present disclosure is not, however, limited to any particular base panel 30 material or configuration. In some embodiments, the biomedical sensor 20 may be described as having rigid regions 32 where the ultrasonic transducers 26 reside, and one or more deformable regions 34 disposed between the rigid regions 32. FIG. 4 illustrates an example of a biomedical sensor 20 that has a first ultrasonic transducer 26A (or array of ultrasonic transducers 26) disposed in a first rigid region 32A, a second ultrasonic transducer 26B (or array of ultrasonic transducers 26) disposed in a second rigid region 32B, and a deformable region 34 disposed between and connecting the first and second rigid regions 32A, 32B. In some embodiments, an adhesive is disposed on at least portions of the body panel 30. The adhesive can be any medical grade adhesive that is safe for skin surfaces, and adequate to maintain the ultrasonic transducers 26 in contact with the subject's skin. In those embodiments where the biomedical sensor 20 has rigid regions 32 with ultrasonic transducers 26, the rigid regions 32 may include an adhesive to maintain the ultrasonic transducers 26 in contact with the subject's skin. The present disclosure is not limited to using an adhesive to attach the biomedical sensor 20 to a skin surface; e.g., mechanical fastening systems, or the like may be used. For example, the body panel may be sufficiently stretchable so as to produce a self-adherent effect to the subject's skin.

The displacement sensors 28 are configured to sense and produce information regarding the magnitude and/or orientation of displacement of ultrasonic transducers 26 from their default positions within the biomedical sensor 20. The term "displacement" as used herein refers to any change in position and/or orientation of one or more ultrasonic transducers 26 from at least one other transducer 26. For example, and as described herein, a first transducer may be longitudinally separated from a second transducer by a distance "L" when the biomedical sensor 20 is in a default position, and may be displaced by the distance "L+D" when the biomedical sensor 20 is subjected to longitudinal stress. In this example, and assuming the displacement is purely longitudinal, the magnitude of the displacement is the distance "D". As another example, assume a biomedical sensor 20 has a planar default configuration (e.g., the body panel resides in an X-Y plane) and each transducer 26 projects a signal profile that is centered along an axis perpendicular to the planar body panel 30 (e.g., along a Z axis). If the biomedical sensor 20 is subjected to torsional strain, the separation distance between the first and second transducers 26 may remain substantial equal to the default separation distance "L", but the orientation of the transducer signal profile of the first transducer may be angularly skewed from that of the second transducer or vice versa; e.g., the signal profile of one or both the first and second transducers may no longer be centered along the Z axis. In this instance, the displacements sensors are operable to sense any change in the angular orientation of a transducer that would result in the signal profile from that respective ultrasonic transducer 26 deviating from its orientation in the default configuration. These simplistic displacement examples are provided for illustrative purposes. In many applications, a biomedical sensor 20 may be deformed in such a manner that displacement occurs in three dimensions, and/or may include orientation changes of pitch, roll, or yaw, or any combination thereof—and the displacement sensors 28 are configured to detect such displacement. The aforesaid information may be provided to the controller 24 in the form of electronic signals representative of the displacement, or a determinable change in a property (e.g., a change in capacitance, resistance, conductivity, or the like) that is representative of the displacement. The present disclosure may utilize a variety of different displacement sensor 28 types such as, but not limited to, strain sensors, capacitive sensors, conductive/resistive sensors, etc. A biomedical sensor 20 may include a plurality of the same type of displacement sensor 28, or may include different types of displacement sensors 28. To be clear, the displacement sensor(s) 28 are configured to sense and produce information regarding the displacement of ultrasonic transducers 26 (or in some instances elements within a transducer) from their default positions within the biomedical sensor 20, and the term "displacement" refers to any change in position and/or orientation between at least two transducers 26 (or elements). The aforesaid transducers 26 may be individual transducers 26, or a first transducer 26 within a first array and a second transducer 26 in a second array, or first and second transducers 26 within an array, or elements within a transducer 26, at least one of which is displaced from its default position, and therefore displaced relative to the aforesaid second transducer (or element).

Figure 5A:
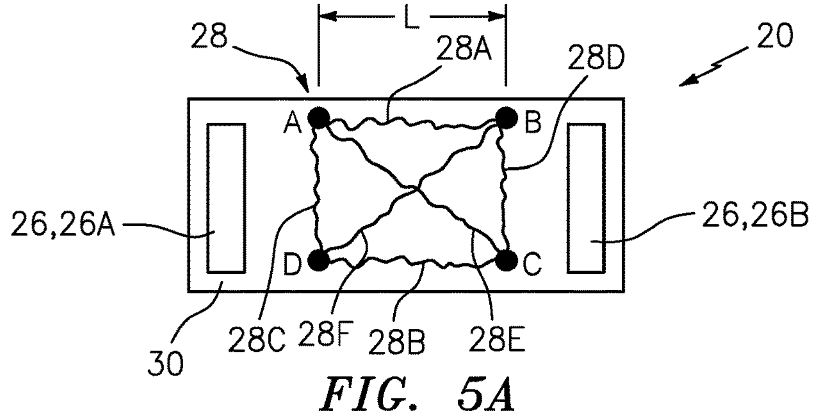
FIG. 5A is a diagrammatic view of a biomedical sensor shown in a default configuration, and illustrating displacement sensors.
Figure 5B:
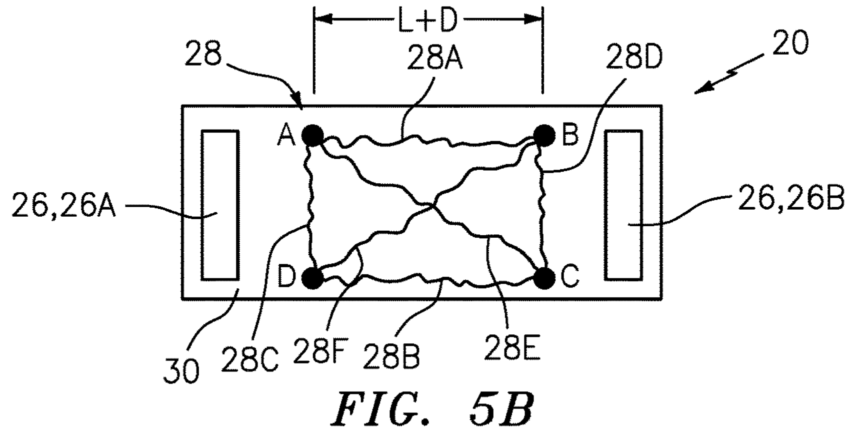
FIG. 5B is a diagrammatic view of the biomedical sensor shown in FIG. 5A, shown in a deformed configuration subject to longitudinal strain.
Figure 5C:
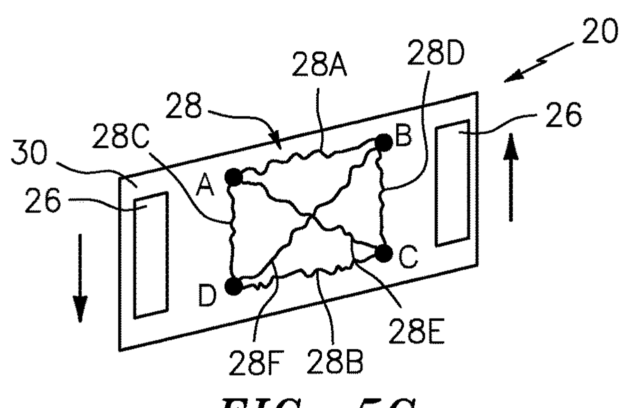
FIG. 5C is a diagrammatic view of the biomedical sensor shown in FIG. 5A, shown in a deformed configuration subject to shear strain.
Figure 5D:
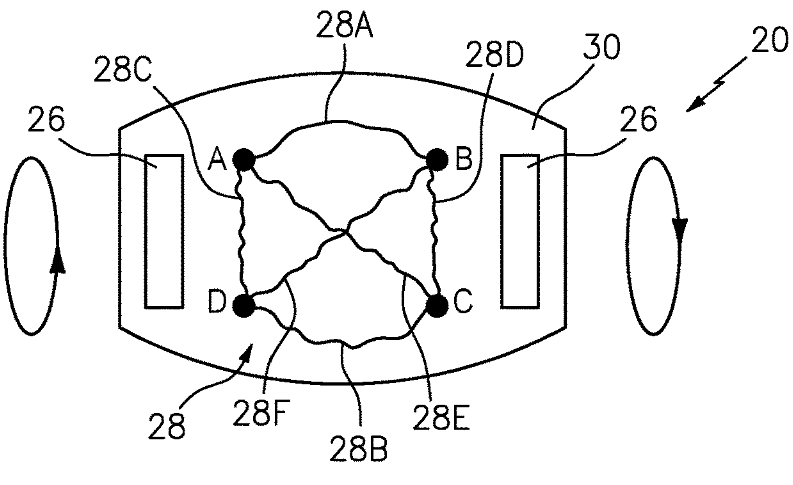
FIG. 5D is a diagrammatic view of the biomedical sensor shown in FIG. 5A, shown in a deformed configuration subject to torsional strain.
Figure 5E:
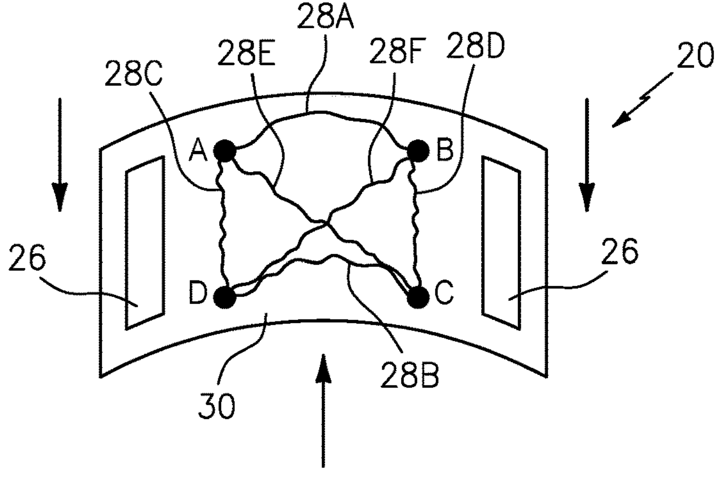
FIG. 5E is a diagrammatic view of the biomedical sensor shown in FIG. 5A, shown in a deformed configuration subject to bending/buckling.

FIGS. 5A-5E diagrammatically illustrate a biomedical sensor 20 embodiment in its default location (FIG. 5A), and the same biomedical sensor 20 subjected to a number of different deformation types to illustrate how displacement sensors 28 may be utilized to sense and produce information regarding the magnitude and/or orientation of ultrasonic transducer 26 displacement from their default positions. The example biomedical sensor 20 shown in FIGS. 5A-5E includes a first strain sensor 28A disposed between points A and B (e.g., extending in a lengthwise direction), a second strain sensor 28B disposed between points C and D (e.g., extending in a lengthwise direction), a third strain sensor 28C disposed between points A and D (e.g., extending in a widthwise direction), a fourth strain sensor 28D disposed between points B and C (e.g., extending in a widthwise direction), a fifth strain sensor 28E extending between points A and C, diagonal to the lengthwise and widthwise directions, and a sixth strain sensor 28F extending between points B and D, diagonal to the lengthwise and directions. FIG. 5B diagrammatically illustrates the biomedical sensor 20 subjected to longitudinal strain. FIG. 5C diagrammatically illustrates the biomedical sensor 20 subjected to shear strain. FIG. 5D diagrammatically illustrates the biomedical sensor 20 subjected to torsional strain. FIG. 5E diagrammatically illustrates the biomedical sensor 20 subjected to bending and/or buckling. The configuration of displacement sensors 28A-28F shown in FIGS. 5A-5E is provided to facilitate the description herein, and the present disclosure is not limited to this particular configuration of displacement sensors 28.

Figure 6A:
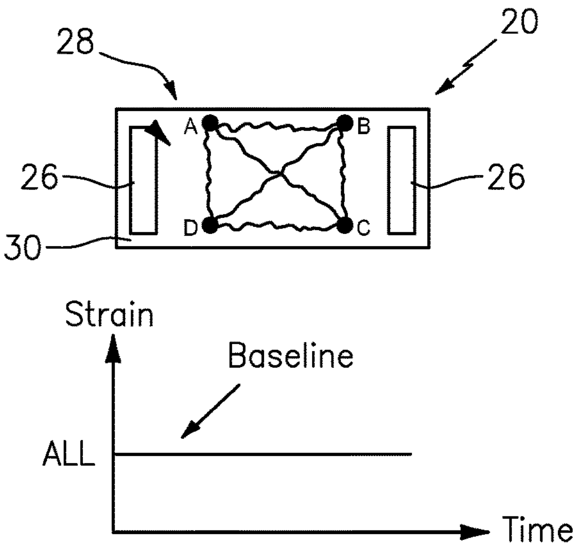
FIG. 6A is a diagrammatic view of a biomedical sensor shown in a default configuration, and a graph of strain versus time, the strain sensed from a plurality of displacement sensors.
Figures 6B, 6C, 7:
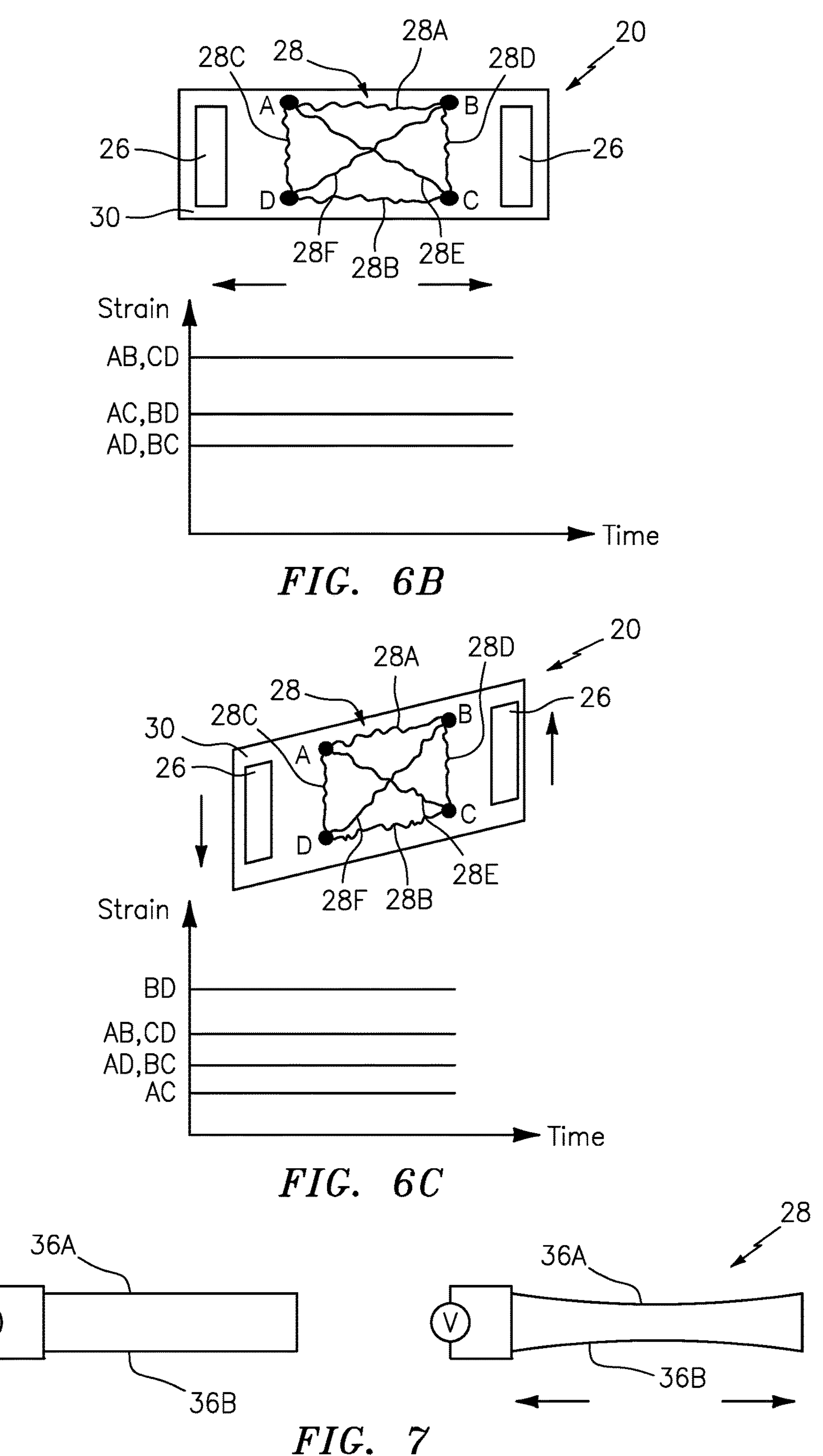
FIG. 6B is a diagrammatic view of a biomedical sensor shown in a deformed configuration subject to longitudinal strain, and a graph of strain versus time, the strain sensed from a plurality of displacement sensors.
FIG. 6C is a diagrammatic view of a biomedical sensor shown in a deformed configuration subject to shear strain, and a graph of strain versus time, the strain sensed from a plurality of displacement sensors.
FIG. 7 diagrammatically illustrates a capacitive displacement strain sensor embodiment.

FIGS. 5A-5E illustrate some, but not all, fundamental deformation types that a biomedical sensor 20 may be subjected to during application to and/or use on a subject. The displacement sensors 28 are preferably configured so that the collective signal information from the respective displacement sensors 28 permits both the type of the deformation to be identified, and the magnitude of the deformation to be measured. This information in turn, permits substantially any change in the position and/or orientation of the ultrasonic transducers 26 from the default position to be determined. In the longitudinal deformation shown in FIG. 5B, for example, the longitudinally disposed displacement sensors (i.e., the first strain sensor 28A, A-B and the second strain sensor 28B, C-D) will sense longitudinal stretching. Because of the orthogonal-like configuration of the displacement sensors 28A-28F, however, the longitudinally disposed displacement sensors 28A, 28B are not the only displacement sensors to sense strain; e.g., the diagonally oriented displacement sensors (fifth strain sensor 28E, A-C, sixth strain sensor 28F, B-D) also sense strain, albeit at a different rate than the longitudinal displacement sensors 28A, 28B. The controller 24 is adapted to receive the displacement sensor signals collectively and determine the type and magnitude of the biomedical sensor 20 deformation, and consequent displacement of the ultrasonic transducers 26. FIGS. 6A-6C diagrammatically illustrate the sensed strain contributions from the various displacement sensors 28 for a biomedical sensor 20 in its default configuration (FIG. 6A), a biomedical sensor 20 subjected to longitudinal strain (FIG. 6B), and a biomedical sensor 20 subjected to shear strain (FIG. 6C). The strain versus time graph shown in FIG. 6A depicts the sensed strain contributions of all of the displacement sensors 28 at a baseline value in the absence of deformation. The strain versus time graph shown in FIG. 6B depicts the sensed strain contributions of the longitudinally disposed displacement sensors (i.e., the first strain sensor 28A, A-B and the second strain sensor 28B, C-D) as sensing a greater amount of strain than the diagonally oriented displacement sensors (fifth strain sensor 28E, A-C, sixth strain sensor 28F, B-D) and the widthwise disposed displacement sensors (third strain sensor 28C, A-D, fourth strain sensor 28D, B-C). The strain versus time graph shown in FIG. 6C depicts the sensed strain contribution of a diagonally oriented displacement sensors (sixth strain sensor 28F, B-D) as sensing a greater amount of strain than the longitudinally disposed displacement sensors (first strain sensor 28A, A-B, second strain sensor 28B, C-D), and the widthwise disposed displacement sensors (third strain sensor 28C, A-D, fourth strain sensor 28D, B-C), and the other diagonally oriented displacement sensor (fifth strain sensor 28E, A-C). In each of these instances, the collective signals from all of the displacement sensors 28 are communicated to the controller 24, and the controller 24 in turn uses the aforesaid signals to determine the type and magnitude of the biomedical sensor 20 deformation, and consequent displacement of the ultrasonic transducers 26.

As stated above, the displacement sensor 28 configuration shown in FIGS. 5A-5E is a non-limiting example provided to facilitate the description herein. The description above makes clear that all of the displacement sensors 28 are likely to sense some amount of strain (e.g., caused by elongation or contraction) in most deformations of the biomedical sensor 20 and that the collective strain signals from the respective displacement sensors 28 can be used to determine the type and magnitude of the biomedical sensor 20 deformation, and consequent displacement of the ultrasonic transducers 26. Other types of deformation (e.g., certain buckling and/or bending modes), however, may not cause displacement sensor 28 elongation or contraction. As will be described herein, some displacement sensor 28 configurations include one or more deformation sensors 28 that are sensitive to bending or buckling deformation.

FIGS. 7-12B illustrate non-limiting examples of displacement sensor 28 types that may be used with the present disclosure. The displacement sensor 28 types may be classified as symmetric (insensitive to bending and/or buckling convexity—e.g., FIGS. 7-10) and asymmetric (sensitive to bending and/or buckling convexity—e.g., FIGS. 11A and 11B).

FIG. 7 diagrammatically illustrates a capacitive displacement strain sensor 28 embodiment. The horizontal surfaces 36A, 36B of the sensor 28 are electrically conductive. Under sufficient longitudinal stress, the displacement strain sensor 28 stretches horizontally, and typically shrinks vertically due to the Poisson effect. As a result, the distance between the horizontal surfaces 36A, 36B is reduced and that alters the capacitance of the displacement sensor 28. Displacement information may be produced by a direct measurement of the capacitance of the displacement sensor 28 via current and voltage values associated with the sensor 28. Alternatively, displacement information may be produced by measuring the resonance frequency of a circuit that includes the capacitive displacement sensor 28.

Figure 8:
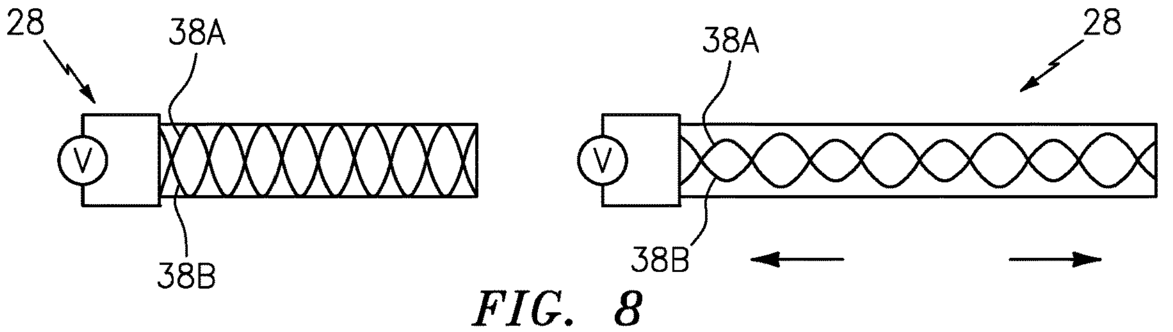
FIG. 8 diagrammatically illustrates a displacement strain sensor embodiment having a pair of interwoven isolated conductors.

FIG. 8 diagrammatically illustrates a displacement strain sensor 28 embodiment having a pair of interwoven isolated conductors 38A, 38B that may offer a substantially greater strain dynamic range. The pair of conductors 38A, 38B have a characteristic impedance. Longitudinal stress alters the pattern of the conductors 38A, 38B and therefore its characteristic impedance. The aforesaid changes in impedance can be used to produce displacement information.

Figure 9A:
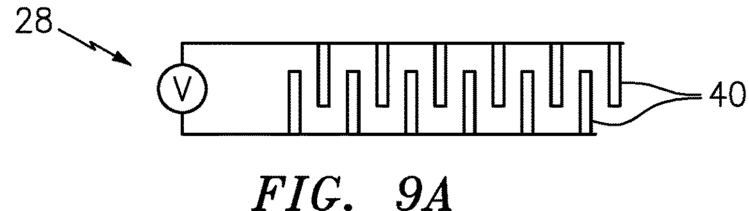
FIG. 9A diagrammatically illustrates a displacement strain sensor embodiment in normal state (no forces applied).
Figure 9B:
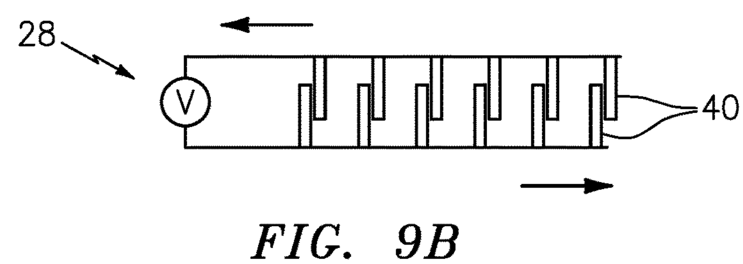
FIGS. 9B-9D diagrammatically illustrate the displacement strain sensor embodiment shown in FIG. 9A with a shear stress load.
Figure 9C:
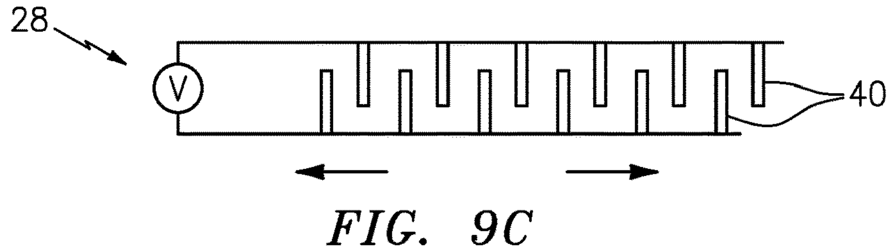
Figure 9D:
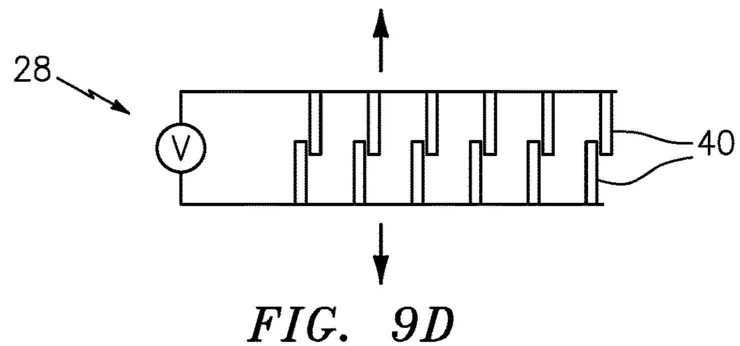

FIGS. 9A-9D diagrammatically illustrate a displacement strain sensor 28 embodiment that includes interdigital elements 40. The capacitance of the sensor 28 is related to the distance between adjacent interdigital elements 40. Hence, the capacitance of the sensor 28 can be altered by changing the interdigital element 40 spacing. This type of displacement sensor 28 is substantially sensitive to shear strain, but also to longitudinal stress in both the vertical and horizontal dimensions of the plane of the displacement sensor 28. FIG. 9A illustrates the displacement strain sensor 28 in a normal state (no forces applied). FIGS. 9B and 9C illustrate the displacement strain sensor 28 with a shear stress load applied (e.g., longitudinal force—shown horizontally). FIG. 9D illustrates the displacement strain sensor 28 with a shear stress load applied (e.g., lateral force—shown vertically).

Figure 10:
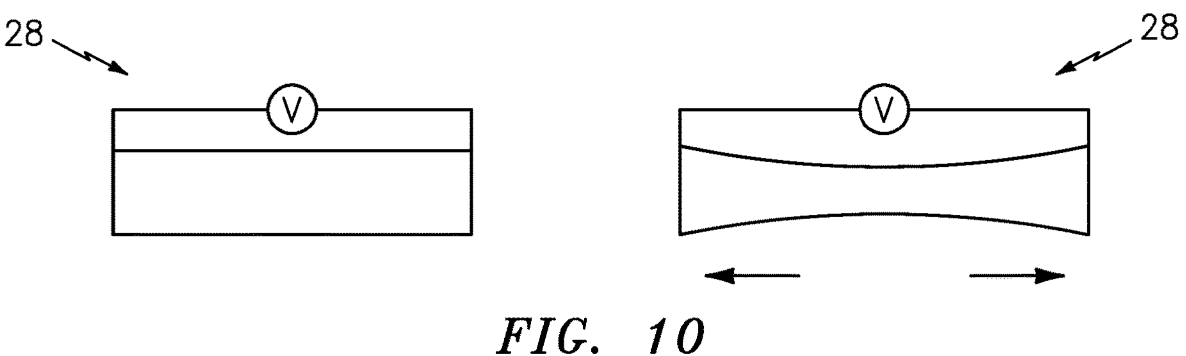
FIG. 10 diagrammatically illustrates an electrically conductive/resistive displacement strain sensor embodiment.

FIG. 10 diagrammatically illustrates an electrically conductive/resistive displacement strain sensor 28. An applied longitudinal force of sufficient magnitude will alter the cross-sectional area and length of the sensor 28, which results in a change of the intrinsic electrical resistance/conductivity of the displacement strain sensor 28.

Figure 11A:
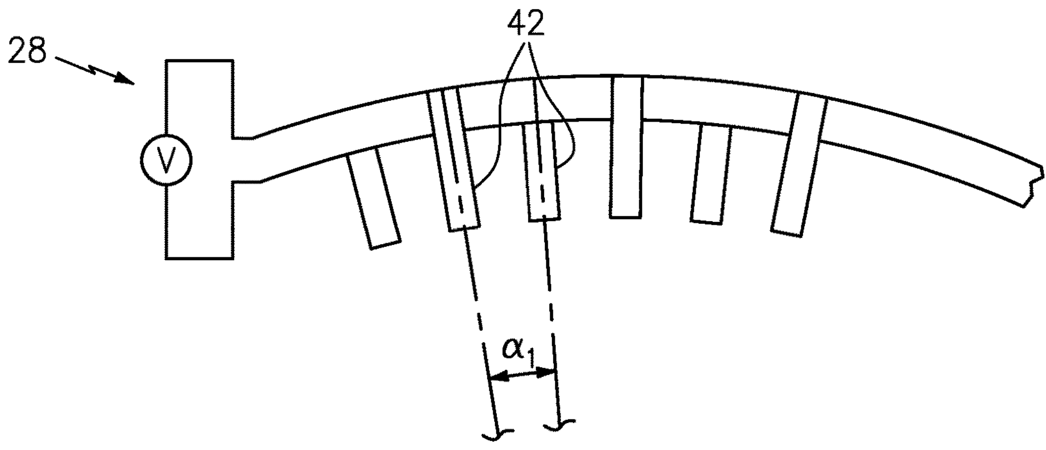
FIGS. 11A and 11B diagrammatically illustrate a capacitive strain sensor with interdigital elements affixed at one common side.
Figure 11B:
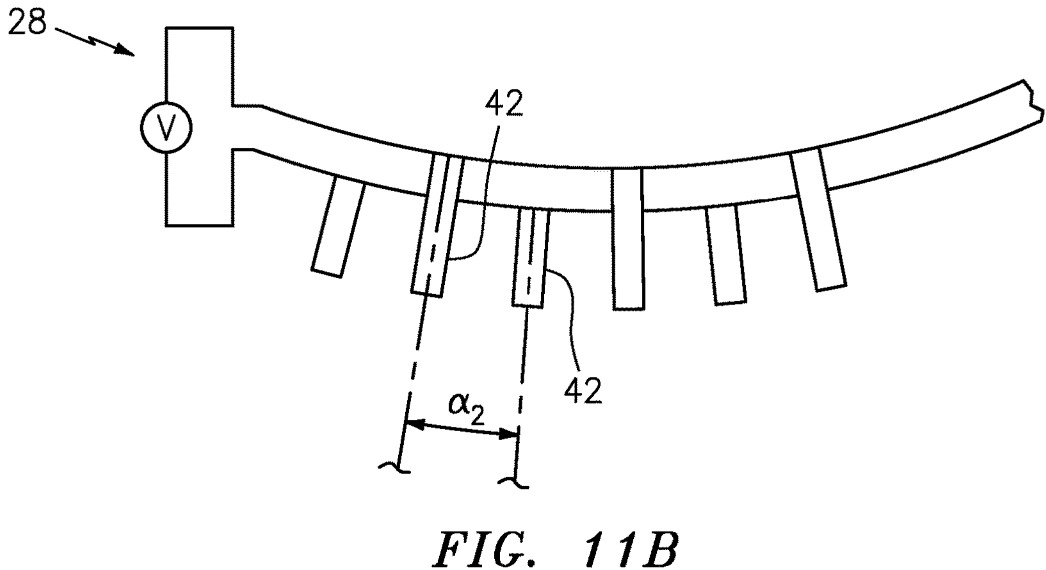

FIGS. 11A and 11B diagrammatically illustrate a capacitive strain sensor 28 with interdigital elements 42 affixed at one common side. As indicated above, this type of displacement strain sensor 28 may be described as being asymmetric and is substantially sensitive to bending and/or buckling and can discriminate between convex and concave bending and/or buckling. FIG. 11A illustrates a first mode of bending where adjacent interdigital elements 42 are angled toward one another at an angle $\alpha_1$ due to the bending mode. FIG. 11B illustrates a second mode of bending where the adjacent interdigital elements 42 are angled away from one another at an angle $\alpha_2$ due to the bending mode, where $\alpha_2$ is greater than $\alpha_1$. The aforesaid changes in interdigital element 42 orientation between adjacent interdigital elements 42 changes the capacitance of the sensor, which in turn can be used to produce displacement information.

Figure 12A:
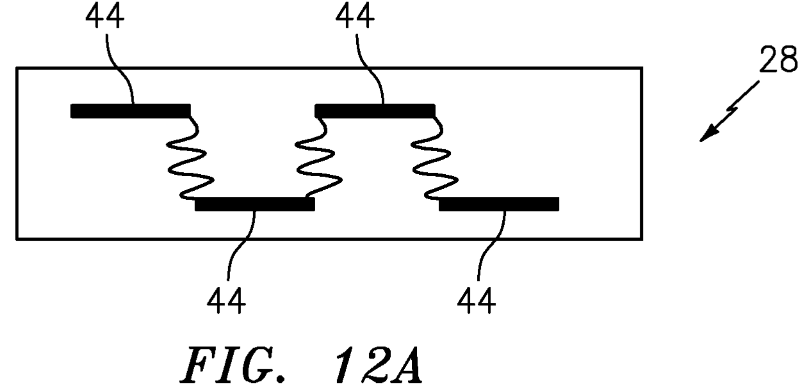
FIGS. 12A and 12B diagrammatically illustrate a displacement sensor embodiment having rigid islands of non-stretchable strain sensors in communication with one another.
Figure 12B:
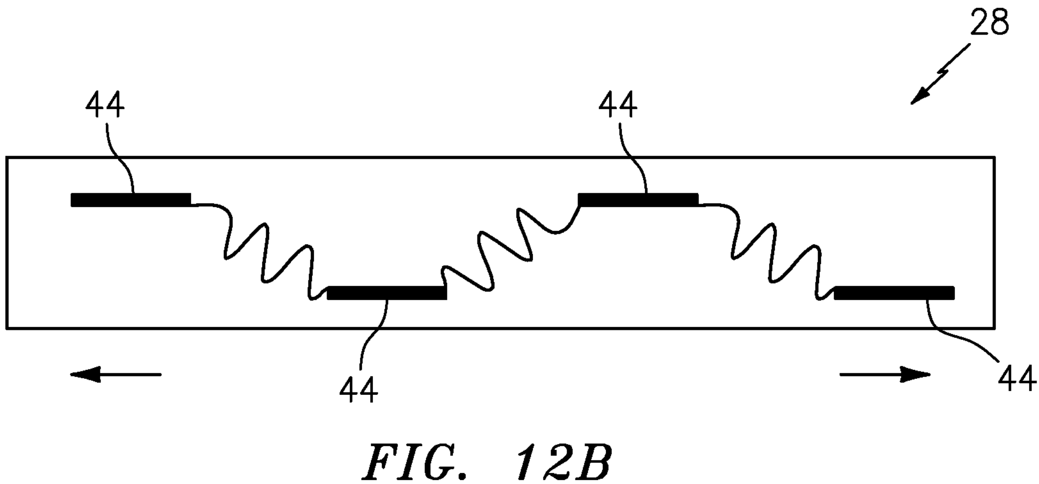

In some embodiments, a displacement sensor 28 may include a plurality of rigid, non-stretchable strain sensors 44 operable to provide information regarding convex and concave bending of the biomedical sensor 20. For example, FIGS. 12A and 12B diagrammatically illustrate a displacement sensor 28 embodiment having rigid islands of non-stretchable strain sensors 44 in communication with one another. FIG. 12A diagrammatically illustrates the displacement sensor 28 with no load applied, and FIG. 12B diagrammatically illustrates the displacement sensor 28 with a longitudinal load applied.

Figure 13A:
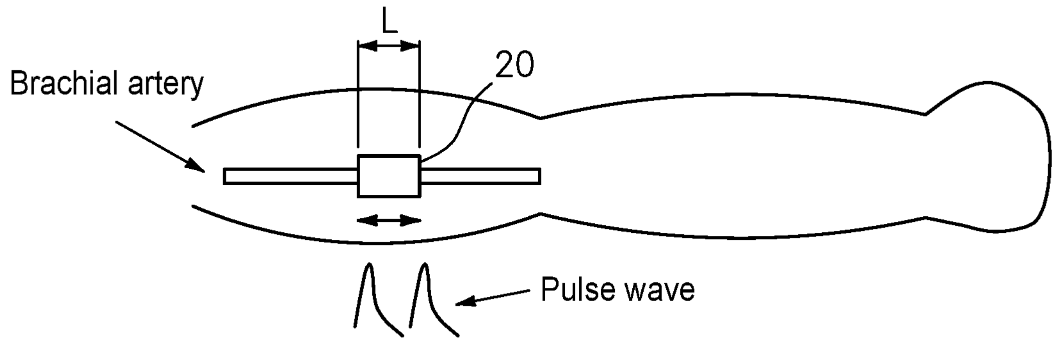
FIGS. 13A and 13B diagrammatically illustrate a biomedical sensor attached to a subject's arm.
Figure 13B:
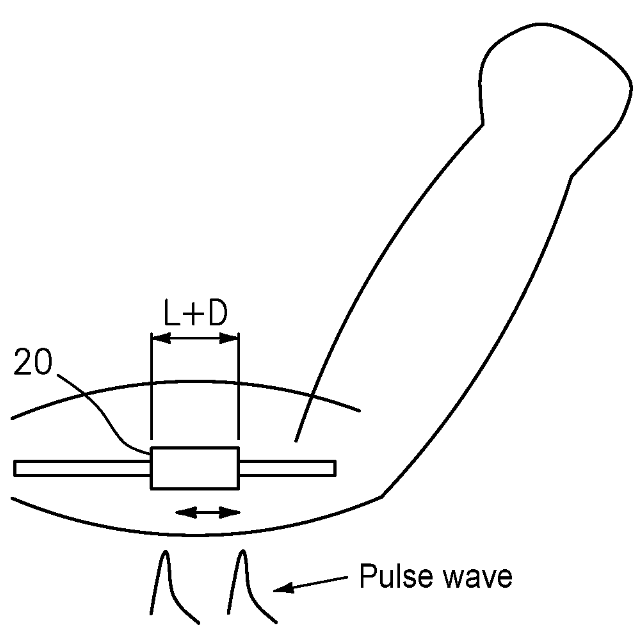

Present disclosure biomedical sensors 20 may be attached to a variety of locations on a subject, such as but not limited to, a leg (proximal to the femoral artery), the abdomen (proximal to the descending aorta artery), and others. To illustrate the utility of the displacement sensors 28 in a particular biomedical sensor 20 application, FIGS. 13A and 13B diagrammatically illustrate a biomedical sensor 20 (e.g., like that diagrammatically shown in FIG. 5A) attached to a subject's arm; e.g., to sense a brachial artery. When attached to the subject's arm and the arm is in a first position (e.g., extended as shown in FIG. 13A), the biomedical sensor 20 will initially be in its default configuration; e.g., as shown in FIG. 5A. When the subject changes arm position (e.g., as shown in FIG. 13B), the biomedical sensor 20 can be subject to longitudinal stress that causes the biomedical sensor 20 to stretch lengthwise/longitudinally; e.g., subjecting the biomedical sensor 20 to longitudinal strain as shown in FIG. 5B. This deformation of the biomedical sensor 20 can cause a positional displacement between ultrasonic transducers 26; e.g., first transducer 26A and second transducer 26B displaced by distance "L" in a default position, and in a deformed configuration are displaced by "L+D", where L+D is greater than L. The change in separation distance between the first and second transducer 26A, 26B (i.e., L vs. L+D)—if unaccounted for—can lead to an error in some physiologic parameters based on the ultrasonic transducer 26 signals. Using the present disclosure, however, displacement sensors 28 disposed in the biomedical sensor 20 provide signal information regarding the amount of transducer 26 displacement from L to L+D to the controller 24.

An example of the importance being able to determine a change in the relative positions of the ultrasonic transducers 26 is evident when the biomedical sensor 20 is used to determine a physiologic parameter such as pulse wave velocity (PWV). PWV measurements are a function of the distance traversed by the pulse wave within the blood vessel. The distance between the ultrasonic transducers 26 within a biomedical sensor 20 is therefore critical in determining the PWV value accurately. Using the example depicted in FIGS. 13A and 13B, the difference in longitudinal distance (L vs. L+D) between transducers 26 can affect a PWV determination. FIG. 13A diagrammatically shows a pair of pulse waves closer together than the pair of pulse waves shown in FIG. 13B, reflecting the difference in distances L and L+D. Hence, using the present disclosure the distance (or any deviation therefrom) can be determined and an error in the PWV measurement can be avoided.

Figure 14:
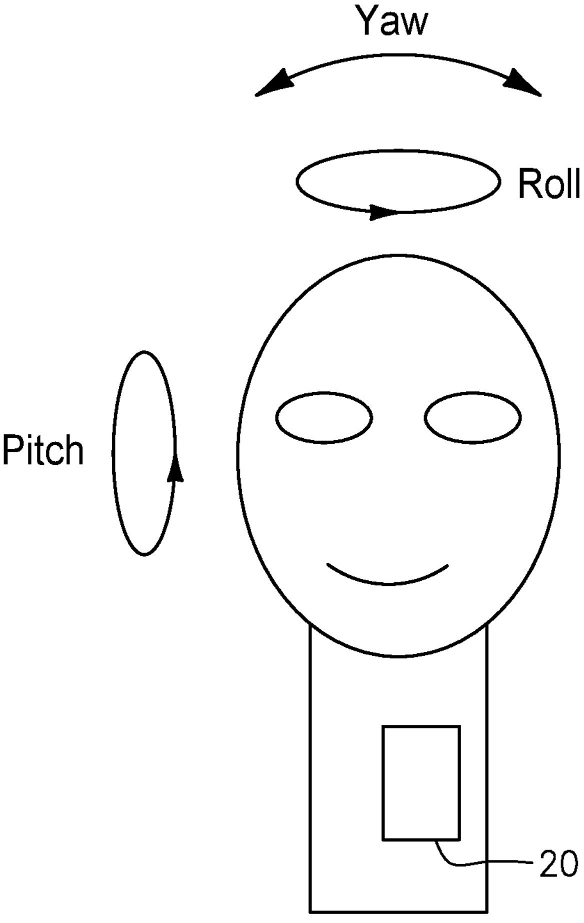
FIG. 14 diagrammatically illustrates a biomedical sensor attached to a subject's neck.

FIG. 14 diagrammatically illustrates a biomedical sensor 20 attached to a subject's neck (e.g., to sense a carotid artery). When a biomedical sensor 20 is placed on a subject's neck (e.g., to sense a carotid artery), the deformation of the biomedical sensor 20 may be substantially more complex that the longitudinal deformation described above; e.g., the deformation may include longitudinal, torsional, or shear stress, and combinations thereof, diagrammatically shown as yaw, roll, and pitch.

Figure 15A:
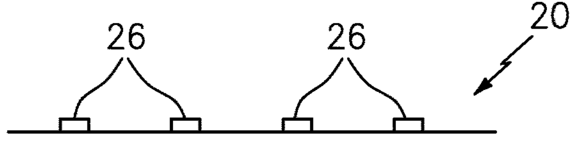
FIG. 15A diagrammatically illustrates an array of ultrasound transducers disposed within a biomedical sensor shown in a planar, default orientation.
Figure 15A:
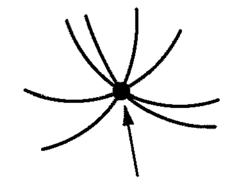
Figure 15B:
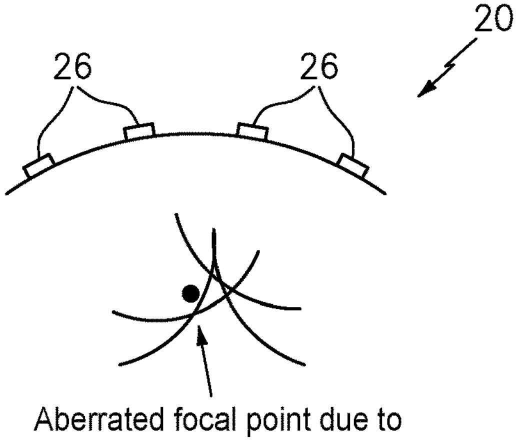
Figure 15C:
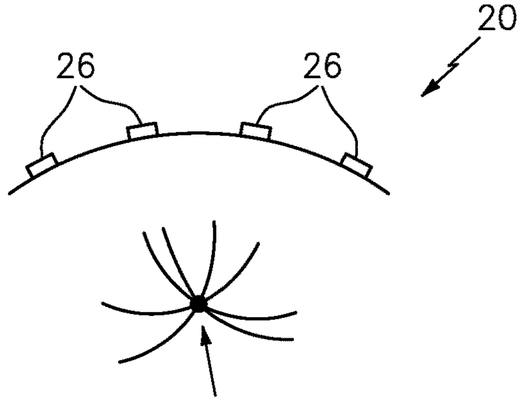

FIGS. 15A-15C provide another example of the significance of the present disclosure, and its ability to measure deformations of the biomedical sensor 20 for the purpose of correcting aberrations of ultrasound measurements. FIG. 15A illustrates an array of ultrasound transducers 26 disposed within a biomedical sensor 20 shown in a planar, default orientation. The signals from the ultrasound transducers 28 are combined following geometrical laws to find focal points corresponding to ultrasound reflectors (e.g., walls within an artery cross-section). FIG. 15B diagrammatically illustrates the biomedical sensor 20 in a configuration deformed from the default configuration. In the deformed configuration, absent the present disclosure, the focal point determined from the ultrasonic transducers 26 will likely be aberrant; e.g., because in the deformed configuration, the relative positions and/or orientations of the ultrasonic transducers 26 are changed from those of the default configuration. Using the teachings of the present disclosure (e.g., using the displacement sensors 28), the type and magnitude of the deformation(s) can be determined, the position and orientation of the ultrasonic transducers 26 can be determined and the accounted for, and a corrected focal point determined; e.g., FIG. 15C.

Figure 16:
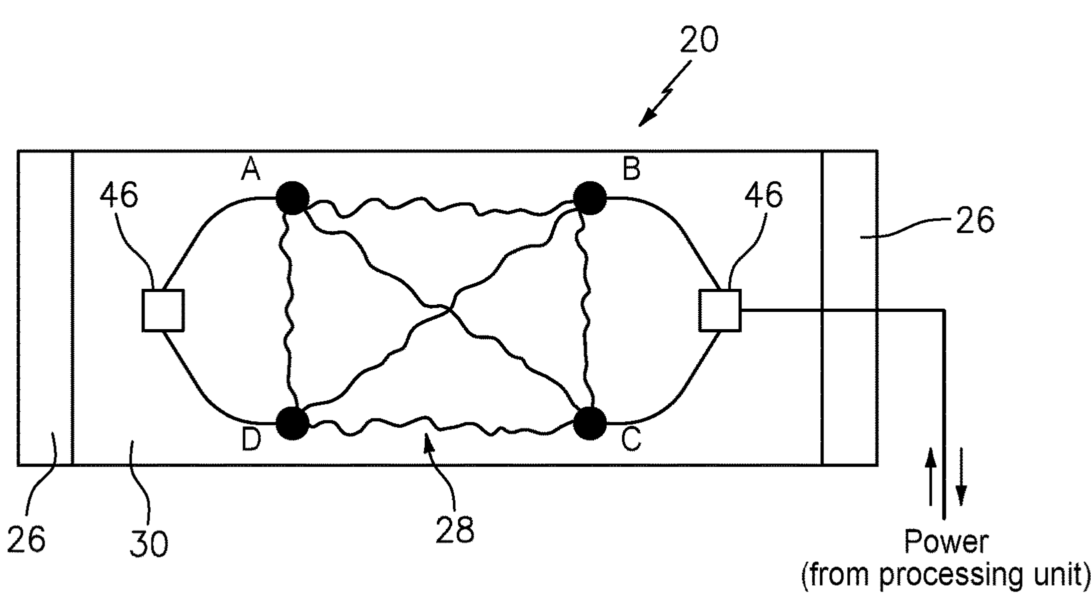
FIG. 16 diagrammatically illustrates a biomedical sensor embodiment configured to perform signal processing locally at the biomedical sensor.
Figure 17:
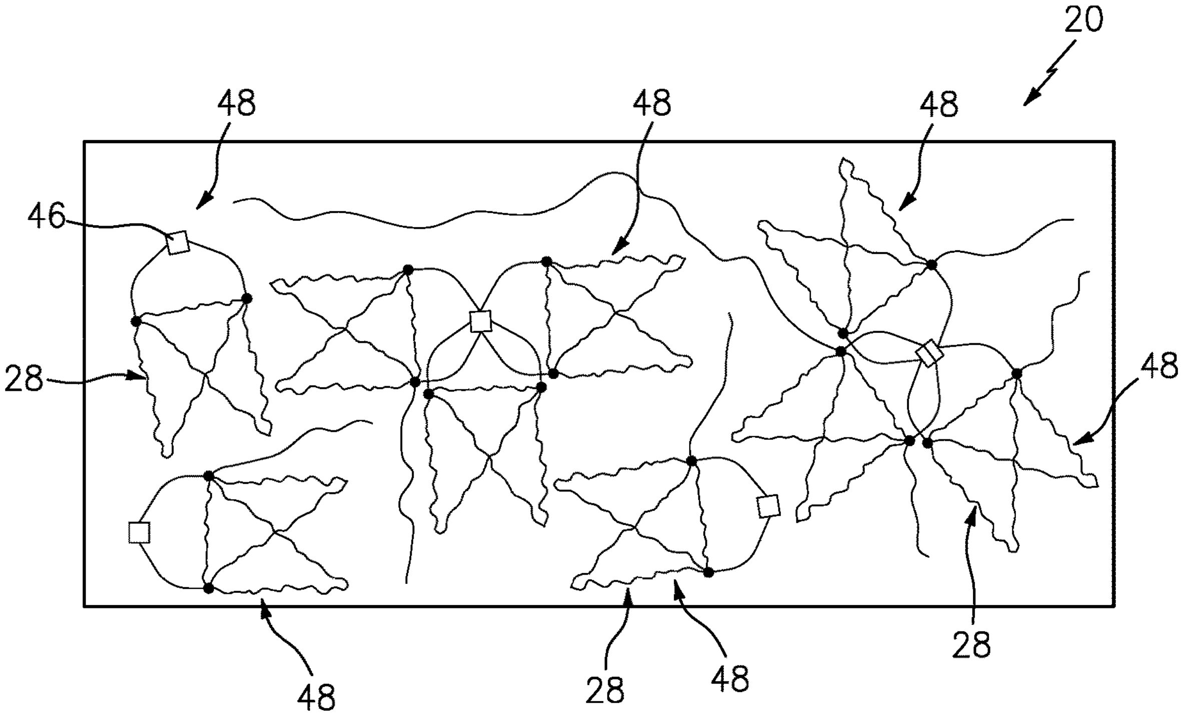
FIG. 17 diagrammatically illustrates a biomedical sensor with a plurality of displacement sensor cells.

Referring to FIGS. 16 and 17, in some embodiments a biomedical sensor 20 may be configured to perform signal processing (e.g., signal multiplexing, conditioning, etc.) locally at the biomedical sensor 20. In those instances where the biomedical sensor 20 is connected by hardwire to the controller 24, a biomedical sensor 20 configured to locally perform signal processing can advantageously limit the number of wires required for communications between the biomedical sensor 20 and the controller 24, and/or simplify the displacement sensor 28 wiring within the biomedical sensor 20. For example, a single processor chip 46 may be in communication with a displacement sensor 28 to measure one or more characteristics (e.g., impedance, capacitance, resistance, etc.) of that particular displacement sensor 28. In some embodiments, one or more processor chips 46 may be included that are operable to perform multiplexing tasks; e.g., a processor chip 46 may be in communication with a plurality of displacement sensors 28 simultaneously, and multiplex computation tasks associated with each displacement sensor 28. These embodiments can advantageously limit the number of wires required for communication between the biomedical sensor 20 and the controller 24, and/or simplify the displacement sensor 28 wiring within the biomedical sensor 20. The power required to operate the processor chips 46 may be provided by the controller 24, or a battery, or other source.

In some embodiments, a biomedical sensor 20 may include a plurality of displacement sensor cells 48. Each cell 48 may be configured as described above with a plurality of displacement sensors 28 configured to sense a variety of different deformations of the biomedical sensor 20, and provide signal information indicative thereof to permit the type and magnitude of the deformation to be identified. In some embodiments, each cell 48 may include one or more processor chips 26. The displacement sensor cells 48 may have a modular configuration; i.e., a pattern that repeats itself, periodic and or symmetric. The present disclosure is not limited to any particular number of displacement sensor cells 48 or relative positions of the same. In fact, present disclosure biomedical sensors 20 can be configured with particular applications (e.g., neck), wherein the number and position of the displacement sensor cells 48 within the biomedical sensor 20 is optimum for that particular application. FIG. 17 diagrammatically illustrates a biomedical sensor 20 with a plurality of displacement sensor cells 48 disposed in an exemplary arrangement.

During operation of at least some present disclosure systems 22, at least one biomedical sensor 20 is attached to the subject. In some instances, the biomedical sensor 20 may be positioned in alignment with a blood vessel of the subject. Non-limiting examples of blood vessels that may be sensed include the descending aortic artery, a carotid artery, a femoral artery, and a brachial artery. When initially attached to the subject, the biomedical sensor 20 may be disposed in its default configuration (e.g., See FIG. 13A) or it may be disposed in a deformed configuration (e.g., See FIG. 14). In some instances, the configuration of the biomedical sensor 20 may change after attachment to the subject (e.g., See FIG. 13B).

Once the biomedical sensor 20 is attached to the subject, the present disclosure permits a determination regarding whether the biomedical sensor 20 is in its default configuration. If the biomedical sensor 20 is determined to be in a deformed configuration, the present disclosure permits a determination of the type and magnitude of the deformation. This determination may be performed once, periodically, or with a frequency so as to be essentially continuous. The determination of the type and magnitude of the deformation may then be used to directly or indirectly determine the position and/or orientation of the ultrasonic transducers 26 and a corresponding correction(s) created so that the information produced by the ultrasonic interrogation is produced more accurately than would be without the correction(s) and one or more physiological parameters (e.g., blood vessel diameter, pulse wave velocity, etc.) are determined more accurately. Hence, the present disclosure discloses an apparatus and method for accounting for three-dimensional (3D) deformations of a biomedical sensor 20 that substantially has a two-dimensional (2D) geometry. Present disclosure biomedical sensors are also not limited for use in determining physiological parameters such as blood vessel diameter, pulse wave velocity, and the like. The ability of the present disclosure to account for three-dimensional (3D) deformations of a biomedical sensor 20 makes it well suited for use in blood flow measurements. A person of skill in the art will recognize that parameters (e.g., blood flow velocity profile, etc.) utilized in determining blood flow measurements may be affected by blood vessel geometry. The ability of the present disclosure to ascertain sensor deformation and account for that deformation, so that the information produced by the ultrasonic interrogation is produced more accurately, can be used to facilitate blood flow measurements.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein. For example, in the exemplary embodiments described above within the Detailed Description portion of the present specification, elements are described as individual units and shown as independent of one another to facilitate the description. In alternative embodiments, such elements may be configured as combined elements.

Additionally, even though some features, concepts, or aspects of the disclosures may be described herein as being a preferred arrangement or method, such description is not intended to suggest that such feature is required or necessary unless expressly so stated. Still further, exemplary or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

What is claimed is:

1. A biomedical sensor for application to a skin surface of a subject, comprising:
- a deformable body panel configured to be placed in contact with the skin surface of the subject;
- at least one first ultrasonic transducer attached to the deformable body panel;
- at least one second transducer attached to the deformable body panel; and
- at least one displacement sensor in communication with the deformable body panel and configured to sense deformation of the deformable body panel;
- wherein the biomedical sensor is disposable in a default configuration wherein the deformable body panel is disposed in a non-deformed state when the biomedical sensor is not applied to the skin surface of the subject, and in the non-deformed state the at least one first ultrasonic transducer and the at least one second ultrasonic transducer are disposed relative to one another in a known first spatial transducer configuration;
- wherein the biomedical sensor is disposable in a deformed configuration in which the deformable body panel is applied to the skin surface of the subject and is deformed and wherein in the deformed configuration the at least one first ultrasonic transducer and the at least one second ultrasonic transducer are disposed relative to one another in a second spatial transducer configuration different than the known first spatial transducer configuration; and
- wherein the at least one displacement sensor is configured to produce signal information indicative of a difference between the known first spatial transducer configuration and the second spatial transducer configuration.

2. The biomedical sensor of claim 1, wherein the at least one displacement sensor includes a plurality of displacement sensors configured to sense a difference between relative positions of the at least one first ultrasonic transducer and the at least one second ultrasonic transducer within the known first spatial transducer configuration, and relative positions of the at least one first ultrasonic transducer and the at least one second ultrasonic transducer within the deformed configuration.

3. The biomedical sensor of claim 1, wherein the biomedical sensor is configured to assume the default configuration when the biomedical sensor is at rest and not applied to the skin surface of the subject.

4. The biomedical sensor of claim 1, wherein the deformable body panel is a solid body.

5. A biomedical system, comprising:
- a biomedical sensor having a deformable body panel, at least one first ultrasonic transducer attached to the deformable body panel, at least one second transducer attached to the deformable body panel, and a displacement sensor in communication with the deformable body panel, wherein the displacement sensor is configured to sense deformation of the deformable body panel;
- wherein the biomedical sensor is disposable in a default configuration wherein the deformable body panel is disposed in a non-deformed state when the biomedical sensor is not applied to a skin surface of a subject, and in the non-deformed state the at least one first ultrasonic transducer and the at least one second ultrasonic transducer are disposed relative to one another in a known first spatial transducer configuration;
- wherein the biomedical sensor is disposable in a deformed configuration in which the deformable body panel is applied to the skin surface of the subject and is deformed and wherein in the deformed configuration the at least one first ultrasonic transducer and the at least one second ultrasonic transducer are disposed relative to one another in a second spatial transducer configuration different than the known first spatial transducer configuration; and
- wherein the displacement sensor is configured to produce signal information indicative of a difference between the known first spatial transducer configuration and the second spatial transducer configuration; and
- a controller in communication with the biomedical sensor and a memory storing instructions, which instructions when executed cause the controller to:
  - determine the difference between the known first spatial transducer configuration and the second spatial transducer configuration using the signal information from the displacement sensor; and
  - produce information representative of the relative positions of the at least one first ultrasonic transducer and the at least one second ultrasonic transducer within the deformed configuration using the determined difference.

6. The system of claim 5, wherein the instructions when executed cause the controller to produce information representative of the relative orientations of the at least one first ultrasonic transducer and the at least one second ultrasonic transducer within the deformed configuration using the determined difference.

7. The system of claim 5, wherein the at least one biomedical sensor is configured to assume the default configuration when the biomedical sensor is at rest and not applied to the skin surface of the subject.

8. The system of claim 5, wherein the instructions when executed cause the controller to produce information relating to blood vessel diameter, or pulse wave velocity, or both, using the information representative of the relative positions of the at least one first ultrasonic transducer and the at least one second ultrasonic transducer within the one or more deformed configurations.

9. A method of using a deformable biomedical sensor, comprising:

providing a biomedical sensor having a deformable body panel, at least one first ultrasonic transducer attached to the deformable body panel, at least one second transducer attached to the deformable body panel, and a displacement sensor in communication with the deformable body panel, wherein the displacement sensor is configured to sense deformation of the deformable body panel, and wherein the biomedical sensor is disposable in a default configuration wherein the deformable body panel is disposed in a non-deformed state when at rest and prior to application to a skin surface of a subject, and in the non-deformed state the at least one first ultrasonic transducer and the at least one second ultrasonic transducer are disposed relative to one another in a known first spatial transducer configuration;

attaching the biomedical sensor to a skin surface of the subject in an applied configuration, wherein in the applied configuration the at least one first ultrasonic transducer and the at least one second ultrasonic transducer are disposed relative to one another in a second spatial transducer configuration;

using the displacement sensor to determine any difference between the first spatial transducer configuration and the second spatial transducer configuration; and producing information representative of the relative positions of the at least one first ultrasonic transducer and the at least one second ultrasonic transducer within the deformed configuration using the determined difference.

* * * * *